United States Patent [19]
Bell

[11] Patent Number: 6,039,696
[45] Date of Patent: Mar. 21, 2000

[54] METHOD AND APPARATUS FOR SENSING HUMIDITY IN A PATIENT WITH AN ARTIFICIAL AIRWAY

[75] Inventor: Craig J. Bell, E. Swanzey, N.H.

[73] Assignee: Medcare Medical Group, Inc., East Swanzey, N.H.

[21] Appl. No.: 08/962,019

[22] Filed: Oct. 31, 1997

[51] Int. Cl.⁷ ..................................................... A61N 5/00
[52] U.S. Cl. ..................................... 600/532; 128/204.21
[58] Field of Search ........................... 600/300, 529–538; 128/204.21, 204.22, 204.23

[56] References Cited

U.S. PATENT DOCUMENTS

| | | | |
|---|---|---|---|
| 3,565,072 | 2/1971 | Gauthier | 128/200.16 |
| 3,831,707 | 8/1974 | Takeuchi | 180/99 |
| 4,366,821 | 1/1983 | Wittmaier et al. | 600/532 |
| 4,723,543 | 2/1988 | Beran | 600/532 |
| 4,821,709 | 4/1989 | Jensen | 128/204.21 |
| 5,081,871 | 1/1992 | Glaser | 600/532 |
| 5,365,938 | 11/1994 | Eskela | 600/532 |
| 5,468,961 | 11/1995 | Gradon et al. | 250/343 |

*Primary Examiner*—Cary O'Connor
*Assistant Examiner*—Michael Astorino
*Attorney, Agent, or Firm*—George W. Dishong

[57] ABSTRACT

A method and apparatus for the sensing and reporting the relative humidity, moisture content, and temperature of inspired or delivered gases in a patient with an artificial airway. The apparatus includes a humidity sensing device, incorporated into an adapter that is compatible with and connectable in series to standard artificial airway connections of a patient's breathing circuit. The apparatus also includes a display means which receives signals from the sensing device, translates the signals and displays results as percent relative humidity and/or moisture content (water content per volume of gas delivered). One apparatus is connectable in series with the artificial airway just before the artificial airway enters the patient, or two apparati are connectable, one in the inspiratory branch of a breathing circuit, and one in the expiratory branch of the breathing circuit to monitor both inspired and expired gases in patients on mechanical ventilation or anesthesia. The method includes the use of the humidity sensing device and adapter in patients with an artificial airway. The apparatus and method are used on patients with or without mechanical ventilation. There is also an apparatus having two humidity sensing chambers, one for inspired gas and one for expired gas, each air-flow isolated from the other and each having a separate humidity sensing device such that both inspiratory and expiratory gases are monitored.

29 Claims, 8 Drawing Sheets

METHOD AND APPARATUS FOR SENSING HUMIDITY IN A PATIENT WITH AN ARTIFICIAL AIRWAY

BACKGROUND OF THE INVENTION

1. Field of the Invention

The present invention relates generally to the monitoring of the inspired gases of medical patients and more particularly to a humidity/moisture sensor attachable to a patient in such a manner as to be able to sense moisture in the patient's airway. Additionally, there may be a monitor for displaying measures of humidity in a patient. The invention also relates to a method of monitoring humidity or inspired gases, with the sensing device being used in conjunction with an in-dwelling artificial airway that allows voluntary and/or mechanical respiration to be accommodated.

2. Background and Prior Art

The upper respiratory system—nose, pharynx, larynx, and trachea—provides the human body with a conditioning means for inspired air. The inspired air is warmed, humidified, and filtered by these structures. The air becomes saturated with moisture that it picks up from the mucus secreted by the goblet cells of the mucus membranes, as it is pulled into the lungs. The warming of the air occurs by the heat exchange that takes place with the extensive capillary bed of the structures of the upper respiratory system.

When a person requires an artificial airway—endotracheal tube, tracheostomy tube, etc.—the functions of the upper respiratory system are bypassed. This means that no matter whether spontaneous breathing is occurring or mechanical ventilation is being provided, the temperature and moisture content of the inspired or delivered gas is not going to be physiologic without artificial conditioning. The technologies to warm and moisten the inspired gas—cascade humidifiers, bubblers, sonic, HME's (Heat and Moisture Exchangers) are well known in the art.

The problem with which clinicians are faced is how to determine and accurately regulate the amount of moisture or relative humidity that is being delivered to the air and therefore the patient with an artificial airway. The literature is full of studies and reports of improper inspired gas humidification. The following are some of the complications reported as a result of improper humidification:

Inadequate Humidification can result in:

Heat loss, Visidity of secretions, Increase in tracheal tube plugging, Atelectsis (mucus plugs), Epithelial damage, Increase in infection rates, Destruction of cilia, and Decrease in surfactant.

Excessive Humidification can result in:

Water intoxication, Atelectasis (water droplets), Inhibition of surfactant production, and Pyrexia (fever).

The current way that clinicians are tracking the amount of moisture being delivered to a patient is through observations of water level changes in a humidifier reservoir per the time interval and the gas flow being delivered. What they do not take into account is losses that occur through condensation in the breathing tubing and due to temperature fluctuations. When a heated wire system is used there is no condensation, but the danger with using a heated wire is delivering dry gas unknowingly, because of the inherent lack of condensate as a visual indicator that some moisture is being delivered (there is never condensate with this method so its presence or amount can not be used as an indicator).

Heat and moisture exchanger (HME's) devices are passive devices to conserve the patient's own heat and moisture from the expired breath. These devices vary in performance which is specified as the moisture per gas volume delivered at select flow rates as tested in the laboratory under controlled conditions. The literature reports that there is a higher incidence of airway plugging with HME,'s use versus heated humidification.

Complications from inappropriate humidification result in longer overall hospital stays, longer ventilator dependency, longer time in high cost intensive care units, longer utilization of delivery and monitoring devices, and more disposable products consumed. The current state of the art recognizes the importance of proper humidification of inspired gases.

The literature is full of studies that compare the humidifying characteristics of different commercially available moisture generating or retaining devices such as heated humidifiers, heat exchangers, and heat and moisture exchangers. Tarnow-Mordi, in Evidence of Inadequate Humidification of Inspired Gas During Artificial Ventilation of Newborn Babies in the British Isles, The Lancet, Oct. 18, 1986, discloses the use of an electronic hygrometer incorporated into a side stream sampling chamber that requires a means to draw gases off of the breathing circuit into the sampling chamber that houses the humidity sensor. This requires the act of drawing of gases out of the breathing circuit in some manner, and removing the gas from the breathing circuit results in humidity changes and condensation which could lead to inaccurate results and thus inappropriate amounts of moisture being supplied to a patient. He discloses the use of a relatively expensive integral sensor/monitor system that gets exposed to patient contamination and would require resterilization prior to use on another patient.

Ballard, in *Humidification for Ventilated Patients* Intensive and Critical Care Nursing (1992) concludes her 1992 study of cascade water bath humidifiers with the following:

"In summary, humidification of gases for those patients receiving both short and long term ventilation is of paramount importance. It has been stated, 'equipment to monitor humidity is not sufficiently sophisticated to allow accurate breath by breath measurements of humidity in the airways.' (Shelly et. al. 1988) The only guideline for manufacturers of heated humidifiers is the international standard which is felt to be an adequate, rather than optimal humidity." The prior art known to the inventor clearly provides the foundation: 1. that there exists a patient threat with delivering improperly humidified inspired gas and that this is clinically recognized as such; 2. that the state of the art in monitoring the moisture content of the inspired gas is cumbersome, labor-intensive, and inaccurate; 3. that the use of electronic hygrometers have been in side stream placement, expensive, totally reusable units which are exposed to patient contamination, and which have been used for studying humidification device performance.

Because the response time of currently available, cost-effective humidity sensors is less than that required to sense and have recorded or displayed breath by breath (inspiration and expiration) humidity changes, the invention may have an embodiment to monitor and trend the humidity of only the inspired gas, over time, and therefore over many breaths. A typical breath rate is 20 breaths per minute. Using a 1:1 ratio of inspired to expired breath duration, a sensor must respond in less than 1.5 seconds to change, however, a 1:2 ratio is not uncommon where the inspired breath occurs in 1.0 seconds or less. The response of currently available, suitable and cost effective, humidity sensors is approximately 5.0 seconds and thus is too slow to be able to monitor breath by breath. However, since the parameter desired to be measured by the present invention is a trend of the humidity of the inspired breaths, (and the fact that a single dry breath is not damaging to a patient, but dry breaths over time are), monitoring and trending the humidity provides the safeguard required. It is not necessary to be able to monitor and record every breath. Even if the sensor only monitors every third breath, a clinician can see on the monitor very quickly if an overly dry or overly humid trend is developing and can quickly act correctively accordingly (or an automated feedback loop mechanism can adjust humidity if there are, for example 5 readings below a determined threshold humidity level. This will provide medical personnel the ability to tailor the humidification means to the type of ventilatory mode and patient condition without over or under humidifying.

Also, the ability to monitor the humidity of the inspired air will reduce incidence of complications, and reduce the length of hospital stay by insuring appropriate humidification to the lungs. Energy will also be saved by way of reduced energy requirements per patient by reducing time on a ventilator, intensive care monitoring, intensive care testing, and the reduced disposable products used. The present invention solves the problems of not being able to measure, monitor, or deliver humidity of inspired or delivered air in patients having an artificial airway. The invention provides better patient care and comfort, reduced medical cost, convenience, and infection control with a disposable sensor, and reduces the energy impact of a patient with an artificial airway.

For the most part, presently, the appropriate humidity is not being delivered to patients having artificial airways. Currently there is no means or system to continually monitor and trend humidity at a patient's artificial airway. It would be advantageous to be able to measure, monitor and deliver appropriate humidity to air inspired by or delivered to a patient with an artificial airway.

SUMMARY OF THE INVENTION

The present invention removes the guesswork from moisture delivery, and helps prevent under or over humidification. In its most basic form, the invention is an apparatus for monitoring humidity in a patient with an artificial airway comprising a humidity sensing device incorporated in the artificial airway in humidity sensing communication with the patient's airflow. I.e., the sensing device may be mounted in, for example, a tube or hose portion of the artificial airway which is attached to the patient. The method to achieve the measuring of humidity in the patient and the manner of making such attachment may be accomplished by simply cutting out a portion of the tube so that a humidity sensing device could be positioned in or over the opening cut in the tube. The sensing device may then be simply "taped" or otherwise secured to the tube in such a manner so that the sensing device can detect the humidity in the airflow to and/or from the patient. The patient's airflow and humidity readings from the humidity sensing device are monitored either periodically or automatically and the caretakers of the patient having the humidity information can take steps to alter the relative humidity or in a more complex system, the humidity can be automatically adjusted for the patient. The present invention provides an inexpensive, single patient apparatus and method to continuously or intermittently monitor the moisture content or relative humidity of the gas inspired by or delivered to a patient with an artificial airway and a source of controlled air.

A primary aspect of the present invention is to provide a system to monitor the humidity of inspired or delivered gases, in which the system includes an adapter, and a single-patient, multi-use, disposable sensor. There may also be means for connecting the adapter to the breathing circuit, a reusable cable and monitor, and a related method of using the system.

Another primary aspect of the present invention is the provision of either a non-ventilating or ventilating single patient moisture sensing device.

Yet another primary aspect of the present invention is to provide a sensing device that connects either just to the artificial airway or to both the artificial airway and to additionally and also to the breathing circuit of a mechanical ventilator or anesthesia machine.

Still another primary aspect is that the adapter allows the passage of aspirating catheters, including closed and open, and other monitoring catheters which are placed into the respiratory path.

A further primary aspect is for monitor output to be continuous or intermittent, providing information that can be used to improve inspiratory gas humidification conditions without further mathematical manipulation, interpolation, or extrapolation.

A yet further primary aspect is to be able to use the present invention simultaneously with ventilation and aspirating systems.

A still yet further primary aspect is to combine a temperature sensing device with the humidity sensing device in the disposable housing.

Another further primary aspect of the present invention is to incorporate digital liquid crystal displays into a monitor for the relative humidity percent and temperature of the inspired gases which information as to humidity and temperature may be transmitted to a monitor remote from the patient or the information may be displayed substantially at or on the patient. The monitor may be an integral part of the adapter.

An aspect of the invention is to provide an apparatus for sensing the humidity of gases present in a patient having an artificial airway. The apparatus comprises an adapter having at least one humidity sensing chamber; means for connecting the adapter to the artificial airway such that the humidity sensing chamber is in gas flow communication with the artificial airway; and a humidity sensing device incorporated into at least one humidity sensing chamber in humidity sensing communication with the gases. The humidity sensing device may comprise a humidity sensing element contained in a sensor housing. The means for connecting the adapter to the artificial airway may be a connection configured to be compatible with a standard artificial airway connection and the means for attaching the adapter to the ventilation circuit may be a connection configured to be compatible with a standard ventilation circuit connection. Where the patient is being ventilated, there is provided a means for attaching the adapter to the ventilation circuit.

Another aspect of the invention is to provide the apparatus with means for communicating humidity information from the humidity sensing element. The humidity information communicated from the humidity sensing device may be in the form of signals which may be electrical, light (such as infrared light) and/or radio frequency types of signals. The means for communicating humidity information from the humidity sensing element may be electrical contacts for electrically connecting each of the humidity sensing devices to a means for receiving and translating the humidity information.

Yet another aspect of the invention is to provide the apparatus with the means for receiving and translating th[]e humidity information communicated from the humidity sensing device and reporting the information to a user, such as a medical caretaker of the patient.

Still yet another aspect of the invention is to provide the apparatus further comprising at least one water vapor permeable membrane positioned and attached in a manner to separate the humidity sensing device from the gases one or all of the humidity sensing chamber(s) and such that the humidity sensing device detects the moisture passing through each of the membrane(s).

Yet still another aspect of the invention is to provide the apparatus wherein the humidity sensing device is formed integral with the wall of the adapter.

A further aspect of the invention is to provide the apparatus further comprising at least one temperature sensing device. The at least one temperature sensing device may further comprise:

means for communicating temperature information from the temperature sensing device; and means for receiving and translating the humidity information communicated from the temperature sensing device and reporting to a user.

A yet further aspect of the invention is to provide the apparatus wherein there are two humidity sensing chambers. There is a first humidity sensing chamber and a second humidity sensing chamber. There is also a means for air-flow isolating the first humidity sensing chamber from the second humidity sensing chamber. The means for air-flow isolating may comprise; a dividing portion, a first one-directional valve disposed at the first humidity sensing chamber and a second one-directional valve disposed at the second humidity sensing chamber. The first and second one-directional valve further disposed such that gases pass through the first humidity sensing chamber in one direction and gases pass through the second humidity sensing chamber in an opposite direction. Each humidity sensing chamber has a first humidity sensing device incorporatable into the first humidity sensing chamber and a second humidity sensing device incorporatable into the second humidity sensing chamber. Each chamber may have a humidity sensing device incorporated therein.

A still further aspect of the invention is to provide the apparatus wherein the means for receiving and translating the humidity information further comprises a minimum level humidity alarm and a maximum level humidity alarm wherein said minimum level humidity alarm is sounded when a detected humidity falls below a determined minimum level, and wherein said maximum level humidity alarm is sounded when a detected humidity rises above a determined maximum level.

A yet still further aspect of the invention is to provide the apparatus wherein the means for receiving and translating the humidity information further comprises means to automatically adjust a moisture delivery system such that delivery of moisture to a patient is automatically regulated in response to humidity and moisture content measurements obtained by and from the humidity sensing device.

A still further aspect of the invention is to provide a method for monitoring the humidity of gases in a patient having an artificial airway, the method comprising the steps of: securing an adapter in humidity sensing communication with a patient's artificial airway and with a ventilation circuit, the adapter having at least one humidity sensing chamber therein; attaching at least one humidity sensing device to the adapter; and placing a means for receiving and translating humidity information communicated from each of the humidity sensing device(s) and reporting to a user. The means for receiving and translating receives signals from the humidity sensing device and translates and reports the signals; and monitoring the signals and responding to them to increase or decrease moisture delivered to a patient. There may also be attached at least one temperature sensing device to the adapter to measure the temperature of gases passing through the adapter. The adapter may comprise a first humidity sensing chamber through which inspired or delivered air passes, and a second humidity sensing chamber through which expired air passes, and which second humidity sensing chamber is air-flow isolated from the first humidity sensing chamber. Therefore there may be the additional steps of; attaching a first humidity sensing device to the first humidity sensing chamber, attaching a second humidity sensing device to the second humidity sensing chamber and measuring and reporting, moisture content and relative humidity of air passing through the first and the second humidity sensing chambers such that both the inspiratory and expiratory gases can be monitored. The apparatus is connected in humidity sensing communication along the inspiratory branch of a breathing circuit, and a second of the apparatus is connected in humidity sensing communication along the expiratory branch of the breathing circuit such that both inspired and expired gases are monitored and reported separately.

These and further aspects of the present invention will become apparent to those skilled in the art to which this invention pertains and after a study of the present disclosure of the invention and from the detailed description taken with reference to the accompanying drawings.

DESCRIPTION OF THE PREFERRED EMBODIMENTS

Figure 1:
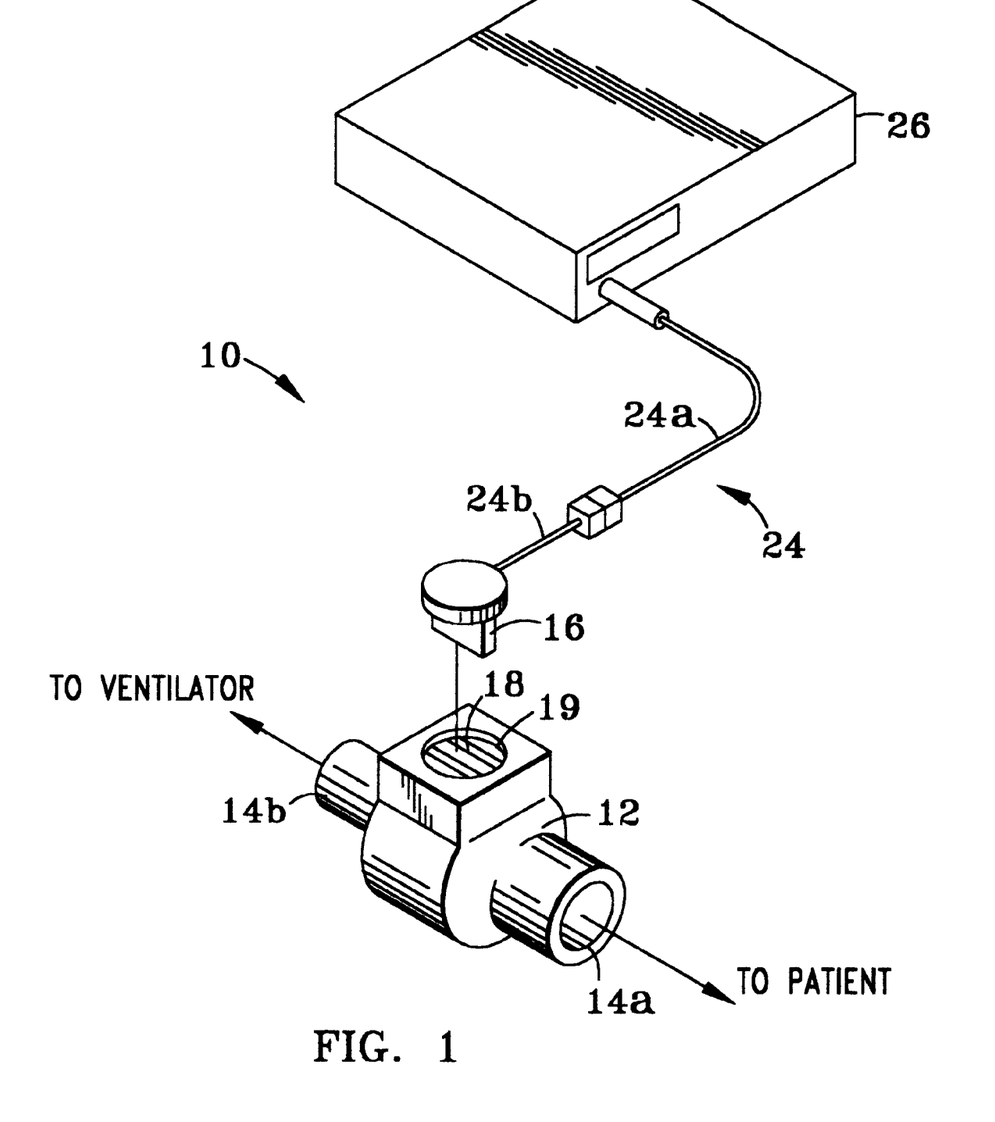
FIG. 1 shows a perspective view of a first embodiment of the invention with an adapter having a disposable, removable humidity sensing device of the present invention in use with a cable and monitor
Figure 2:
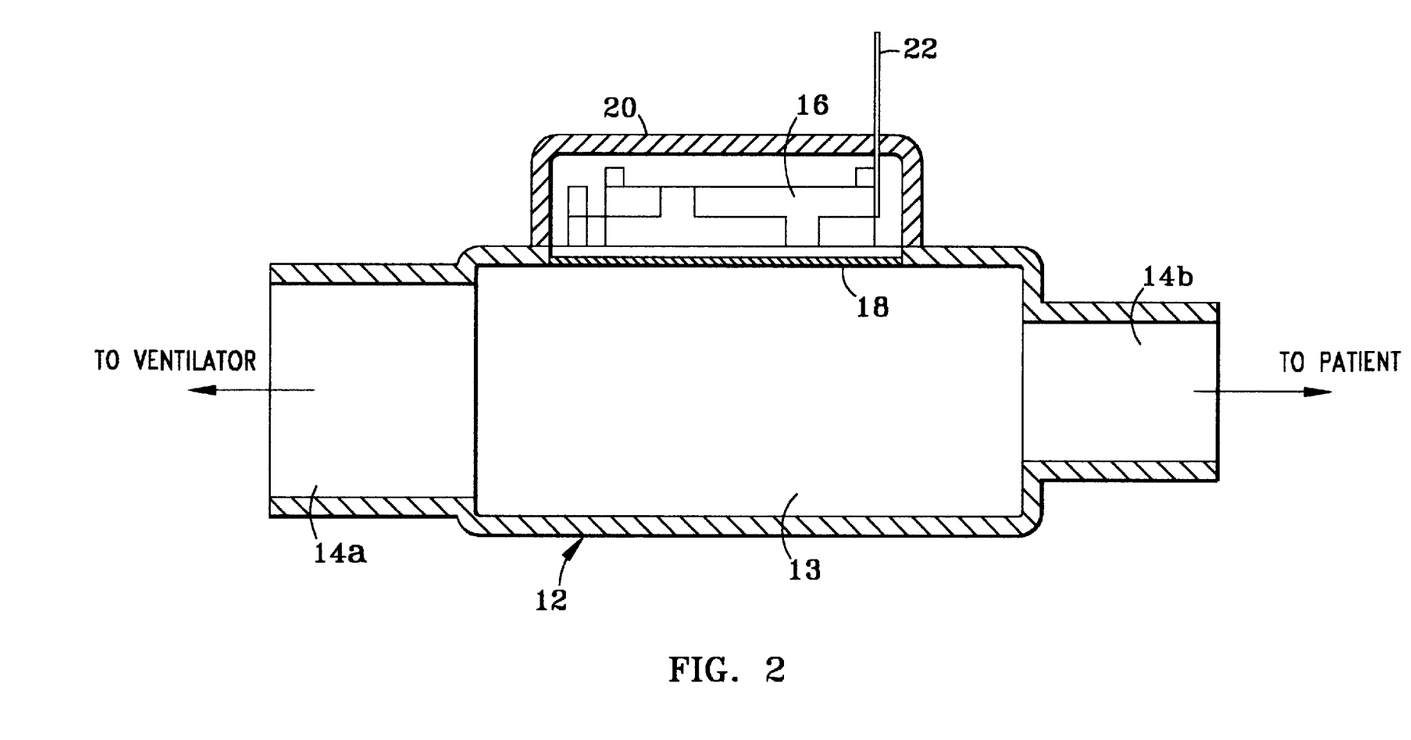
FIG. 2 is a cross sectional view of an adapter having a removable humidity sensing device, and a cap protecting the sensing device.

Referring now in detail to the drawings, in which like reference numerals refer to like elements throughout, one particular embodiment of the apparatus 10 for sensing and reporting the relative humidity of inspired or delivered gases in a patient with an artificial airway and a controlled source of air includes, as shown in FIG. 1, an adapter 12 that is adaptable to be attached or connected in series, or in humidity sensing communication, to the artificial airway of a patient or to the breathing circuit of a patient, if a breathing circuit is being used. In the preferred embodiments, the apparatus would be directly in line in the breathing circuit. In this embodiment, adapter 12 is a one-sensor adapter and has a wall structure which defines a humidity sensing chamber L3, and which is connectable to the artificial airway and breathing circuit by a means for connecting. The means for connecting is preferably by way of a standard 15 or 22 mm female 14a and a standard 15 or 22 mm male 14b luer connection, but may be by other mechanisms such as adhesive connection. Illustrated in all of the figures of this application are axially aligned connections such that the humidity sensing chamber 13 is axially aligned with connections 14a and 14b. Axial alignment is the preferred configuration for the apparatus, but is not necessary. Connections to the artificial airway and breathing circuit of a patient could be at various orientations with respect to the humidity sensing chamber. Adapter 12 may have various geometries, and may be a single piece molded adapter including the connections 14a and 14b, such as that shown in FIGS. 2, 4, and 5, or may be formed from a central portion to which are attached separately formed airway connections 14a and 14b such as that shown in FIGS. 3 and 6. Sensing device 16 preferably comprises a sensor element which is typically contained and, protected in a sensor housing and which has a means for taking the humidity level information from the sensor element and producing and transmitting signals to a means for receiving and translating humidity information communicated from humidity sensing device 16 and reporting to a user, such as monitor 26. In this particular embodiment, a sensing device 16 with an impedance or capacitance based relative humidity (RH) sensor is removably incorporatable or connectable to adapter 12. This removably connectable link allows the removal and replacement of sensing device 16 without breaking the ventilatory or breathing circuit. There may be a selectively water vapor permeable membrane 18 disposed across at least one opening 19 in the wall means of adapter 12 where sensing device 16 is removably connected such that humidity sensing chamber 13 is isolated from the outside and the ventilatory circuit is not interrupted if and when sensing device 16 is removed or replaced. Only water vapor to be detected and reported escapes through membrane 18. Shown in FIG. 1 is one opening 19 which is covered by membrane 18, but instead of adapter 12 having one opening of about the size of sensing device 16, there could be a plurality of smaller openings, in the wall of the adapter, covering a total area about the size of sensing device 16 and which plurality of openings is covered by membrane 18. There may also be a removable cap 20 which covers and protects sensing device 16 where it is attached to adapter 12. The electrical contact or contacts 22 of sensing device 16 protrude from cap 20 to allow connection to a cable 24 and monitor 26. FIG. 2 is an enlarged cross sectional view of adapter 12 with sensing device 16 attached over membrane 18, and protected under cap 20, with electrical contacts 22 protruding from cap 20 for attachment to a monitor or cable.

Figure 3:
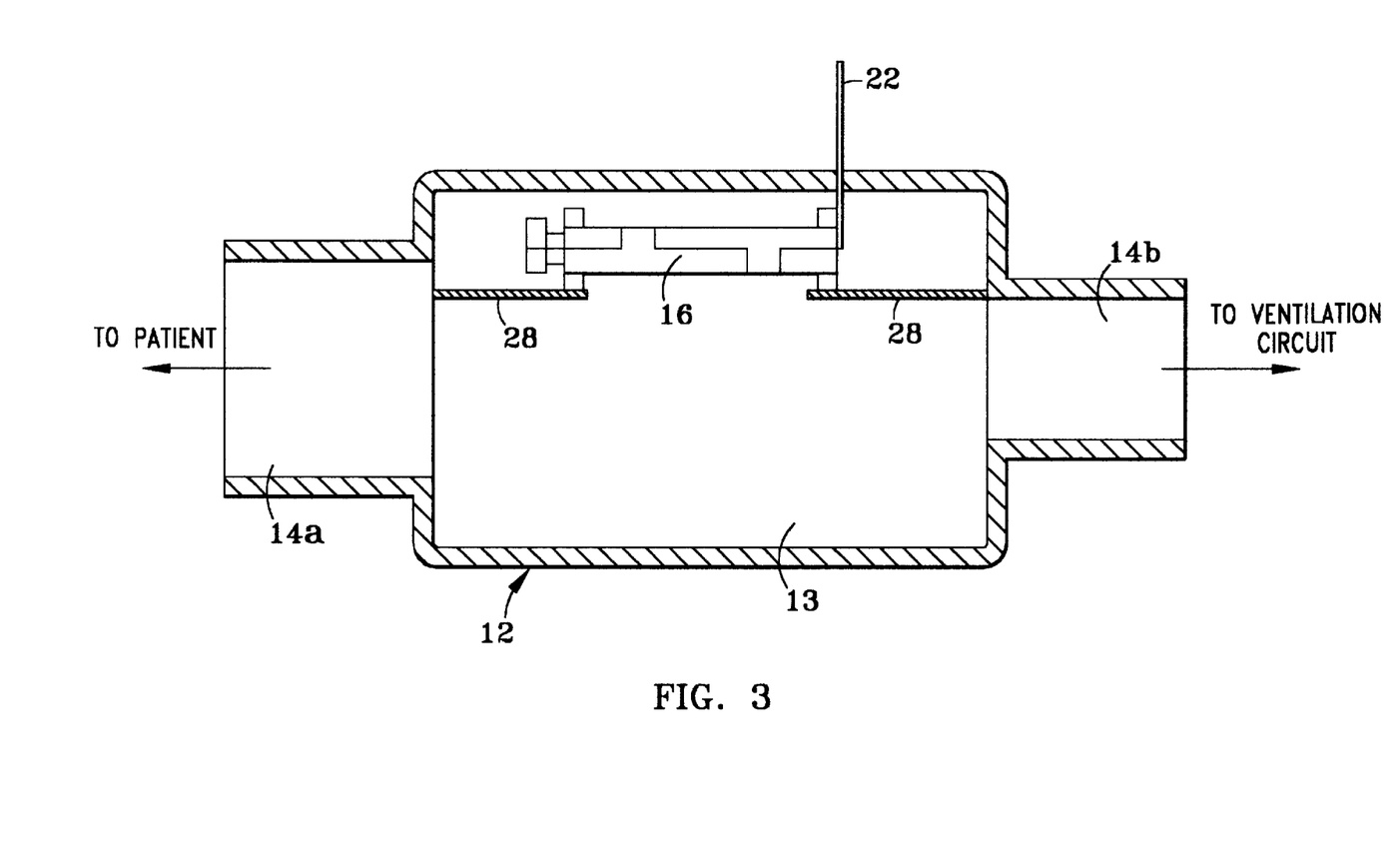
FIG. 3 is a cross sectional view of an adapter having a humidity sensing device attached at an inner surface of the adapter.

Another embodiment, shown in FIG. 3, includes humidity sensing device 16 permanently attached to internal supporting surfaces 28 of adapter 12 such that sensing device 16 detects the moisture content of the gas passing over it, and through adapter 12. In this way, and with all of the preferred embodiments of the invention, readings are taken in the breathing circuit, with no chance for temperature drop or loss of moisture due to condensation before a reading is taken. In this embodiment, the sensing device 16 would be changed every time the artificial airway of the patient is changed, and the breathing circuit of the patient would be interrupted if adapter 12 or sensor 16 were removed.

Figure 4:
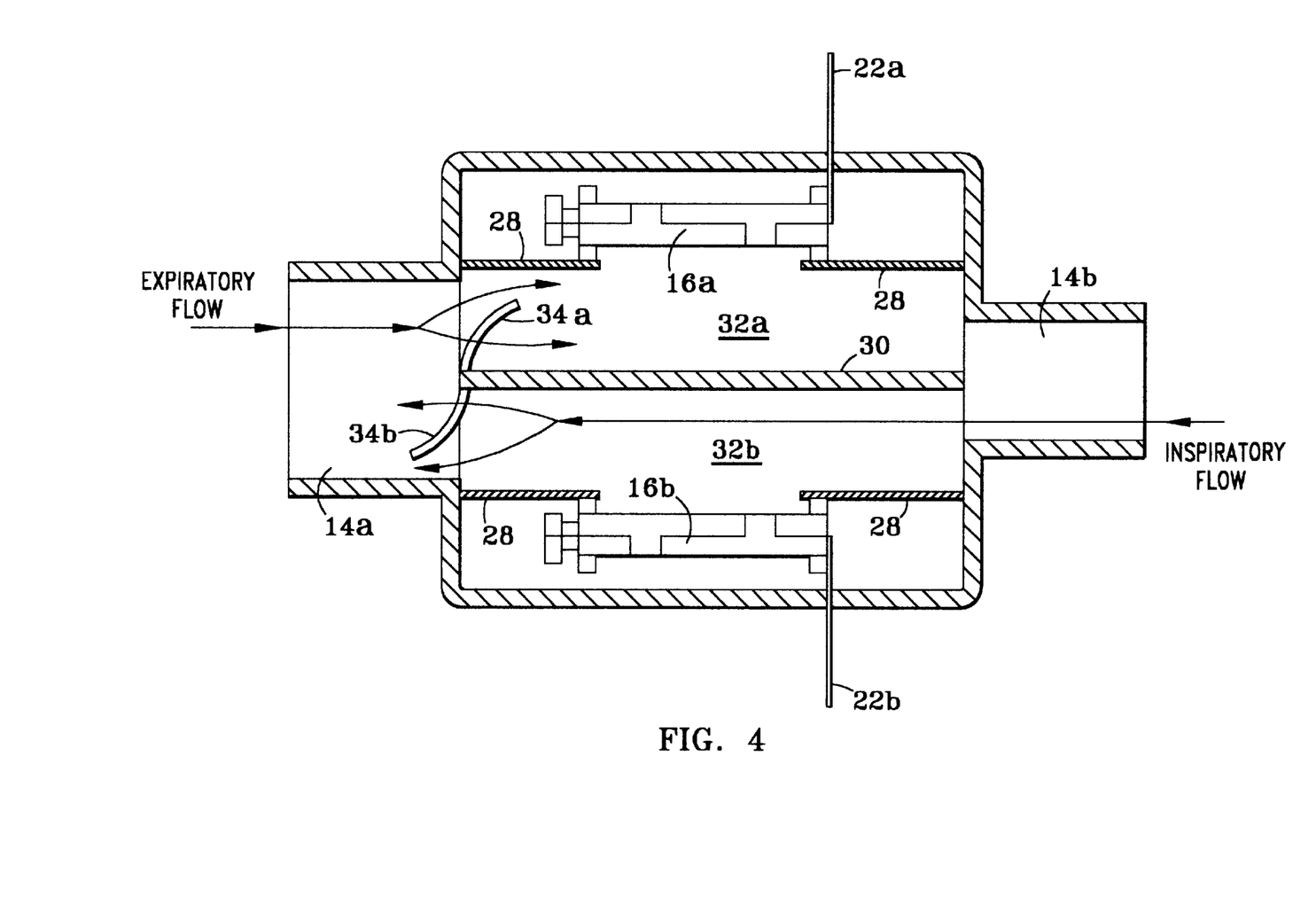
FIG. 4 is a cross sectional view of an adapter having two humidity sensing devices non-removably attached at an inner surface of the adapter, with a central dividing portion and two humidity sensing chambers air-flow isolated from each other by the dividing portion and one-way check valves.

It is also possible to have a two-directional apparatus 12a comprising two sensing devices 16a and 16b incorporatable either removably or permanently attached to two-sensor adapter 12a. As shown in FIG. 4, sensing devices 16a and 16b are permanently attached inside adapter 12a on inner supporting surfaces 28 of adapter 12a and electrical connectors 22a and 22b protrude from adapter 12a. Adapter 12a has a central dividing portion 30 such that two humidity sensing chambers 32a and 32b are created inside adapter 12a, chamber 32a having sensing device 16a and detecting moisture in expired, and chamber 32b having sensing device 16b and detecting moisture in inspired or delivered air. At least one end of each chamber 32a and 32b has a one-way check valve 34a and 34b such that air may only pass in to each chamber in one direction. It is also possible, although not shown, to have one-way check valves at each end of each chamber to further reduce the chance of humidity contamination from air flow of the opposite direction. This embodiment also has means for connecting adapter 12a to the artificial airway and breathing circuit of a patient which may be standard connections such as female and male luer connections 14a and 14b, and which are preferably but not necessarily in axial alignment with humidity sensing chambers 32a and 32b.

Figure 5:
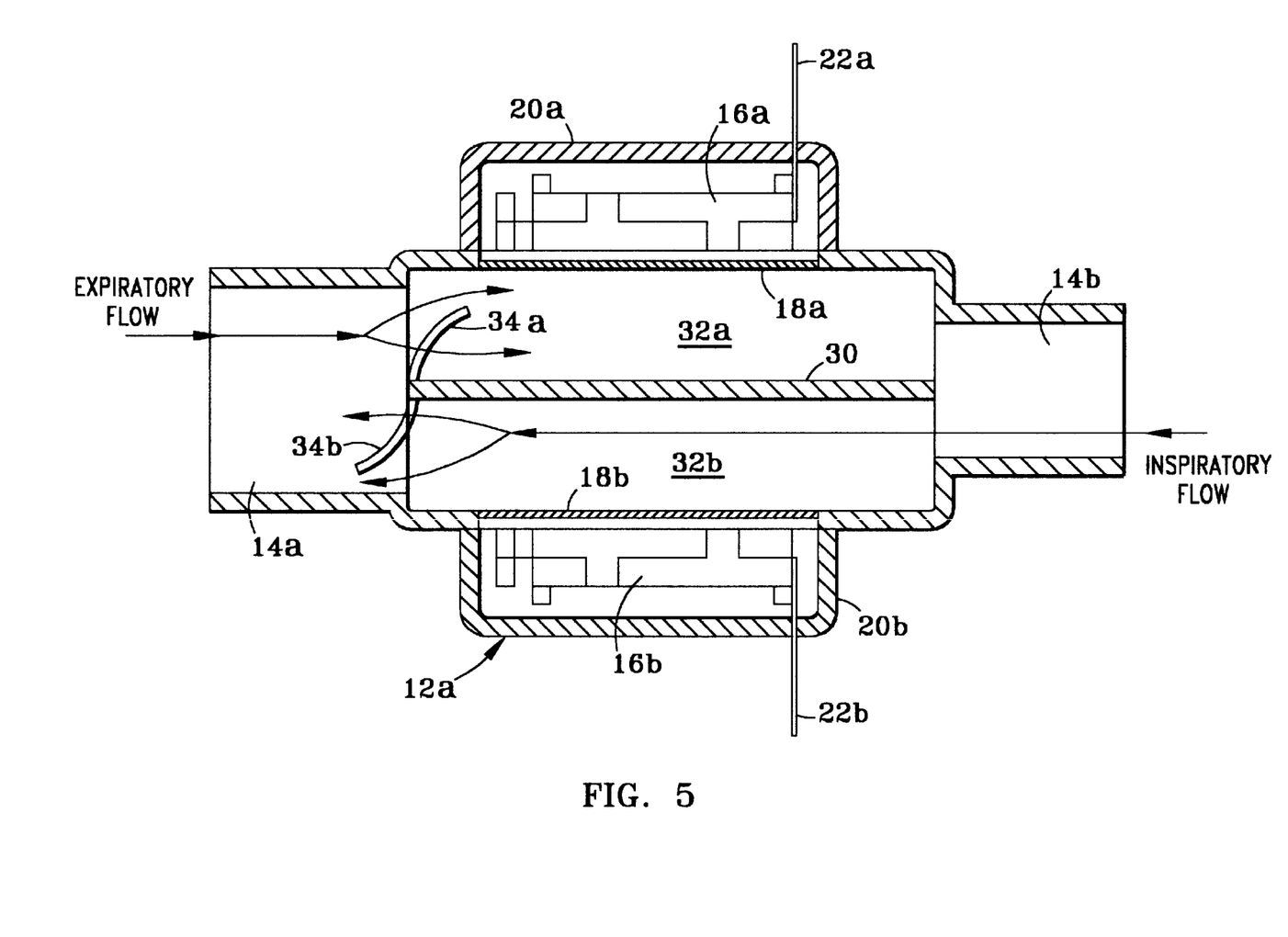
FIG. 5 is a cross sectional view of an adapter having two removable humidity sensing devices.

Sensing devices 16a and 16b could also be removably attached to adapter 12a, protected by caps 20a and 20b, with membranes 18a and 18b covering openings in adapter 12a over which sensing devices 16a and 16b would be placed, as shown in FIG. 5. A two way apparatus such as with adapter 12a could be placed at the proximal end of a patient's artificial airway just before the airway enters the patient such that both inspired or delivered, and expired gases may be trended or monitored with one apparatus.

Figure 6:
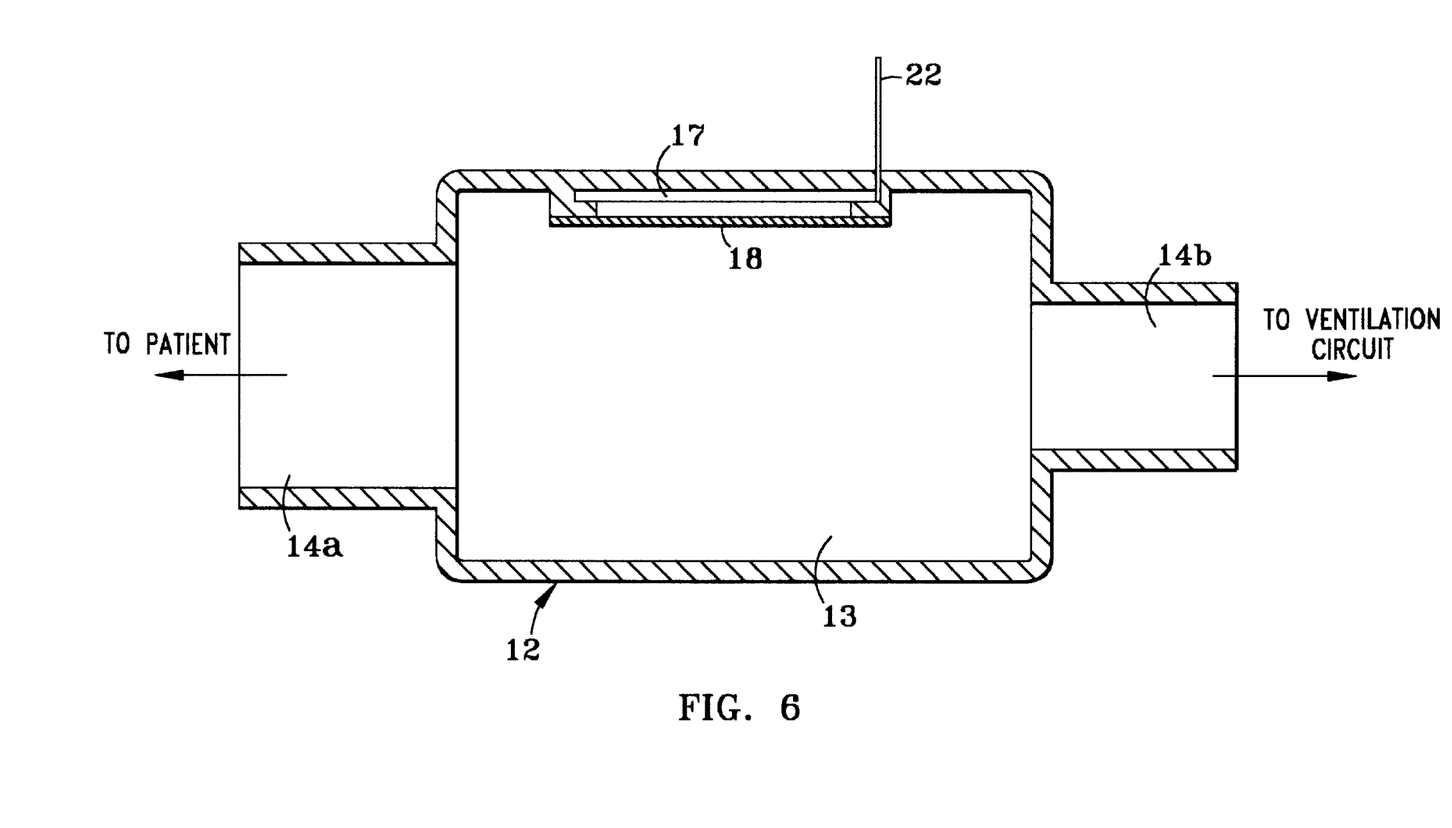
FIG. 6 is a cross sectional view of an adapter having a humidity sensing device formed into the wall structure of the adapter.

Sensing device 16 may also be incorporated into the wall material of the adapter such that the sensor 17 is an integral part of one-sensor adapter 12, and the wall material of adapter 12 essentially forms the sensor housing as shown in FIG. 6. Although not shown, the wall material could completely encase sensor 17 wherein the portion of the wall material facing into the humidity sensing chamber may have a plurality of perforations therethrough for moisture to contact sensor 17. There could be a membrane 18 attached to the supporting wall material to protect sensor 17 from contamination, as shown in FIG. 6, but there need not be any physical barrier between sensor 17 and the interior of humidity sensing chamber 13.

In all embodiments, the sensing device 16 may connect to and communicate with a monitor 26 that may both provide the driving voltage to sensing device 16 and convert the return electrical signal to a readout which is preferably digital but could be analog. Monitor 26 may be AC or battery powered, or AC powered with a battery back-up as the power supply. Monitor 26 may have digital outputs of relative humidity, moisture content, and temperature of inspired and/or expired gases. Monitor 26 is preferably portable.

Monitor 26 may be connectable to electrical contacts 22 of sensing device 16 by way of a reusable cable as shown in FIG. 1. Monitor 26 may also be directly and removably connectable to electrical contacts 22 of sensing device 16, such that monitor 26 may be located at the artificial airway of a patient instead of at some remote location with a cable connection. Monitor 26 may be permanently attached to or incorporated with adapter also so that monitor 26 could be located at the patient's artificial airway, and in this embodiment the sensing device 16 would then be removably attachable to adapter 12 and monitor 26 so that the sensing device 16 could be removed or replaced without interrupting the patient's breathing circuit and the monitor could be reused. The monitor and sensing device configurations may be used with sensing devices 16 that are removable or non-removable from adapter 12 because the monitor 26 may be removable from the sensing device 16 and can be reused, and removed without disturbing the patient's breathing circuit or artificial airway. It is also possible to have a completely integrated adapter, sensing device, and monitor that is disposable.

Currently, humidity sensors are permanently attached to a cord or cable connected to a monitor so there can only be one monitor per patient, and the whole apparatus must be sterilized before use on the next patient. In all of the embodiments of the present invention, the monitor is portable, disconnectable from the sensing device 16, and may be used on more than one patient. The present invention allows realtime, in series trending, tracking of humidity delivered to or inspired by a patient with an artificial airway.

Humidity sensing device 16 may be capable of producing infrared, or radio frequency signals, as opposed to electrical signals, and monitor 26 may be capable of detecting the infrared or radio frequency signals and translating the signals into a visible display, thus eliminating the need for direct, physical connection of monitor 26 to sensing device 16. The information in the electrical signals produced by the humidity sensor or sensing element 17 would be used to encode or modulate, by appropriate circuitry contained either on or incorporated within the humidity sensing element 17 or incorporated as part of the humidity sensing device 16, infrared (or other light frequencies) energy or radio frequency energy which modulated or encoded energy would then be transmitted and subsequently detected and demodulated or decoded by circuitry which would be a part of monitor 26. The source of energy, typically a DC power source, needed to create the transmittable energy could be incorporated into the humidity sensing device or provided to device 16 from an external source.

The interface between sensing device 16 and monitor 26 could be a single cable 24 or cable 24 could be a two part cable connection as shown in FIG. 1, that may comprise a reusable monitor end cable segment 24a that connects to monitor 26 and a relatively short disposable sensor end cable segment 24b permanently attached to sensing device 16. In this way, sensing device 16 and disposable sensor end segment 24b of the cable connection may be disconnected from reusable monitor end segment 24a and monitor 16, such that one monitor 16 may be used for many patients and will not be contaminated. The disposable sensor end cable segment 24b would be low cost and the reusable monitor end cable segment 24a could be of more durable material to allow repeated connecting and disconnecting to the sensor end cable segments of various sensing: devices 16. While it is not shown, there could be a multi-channel monitor which would be attached by cable or in transmittable energy connection to multiple sensing devices such that several patients could be tracked and/or have humidity controlled by the one monitor.

Figure 7:
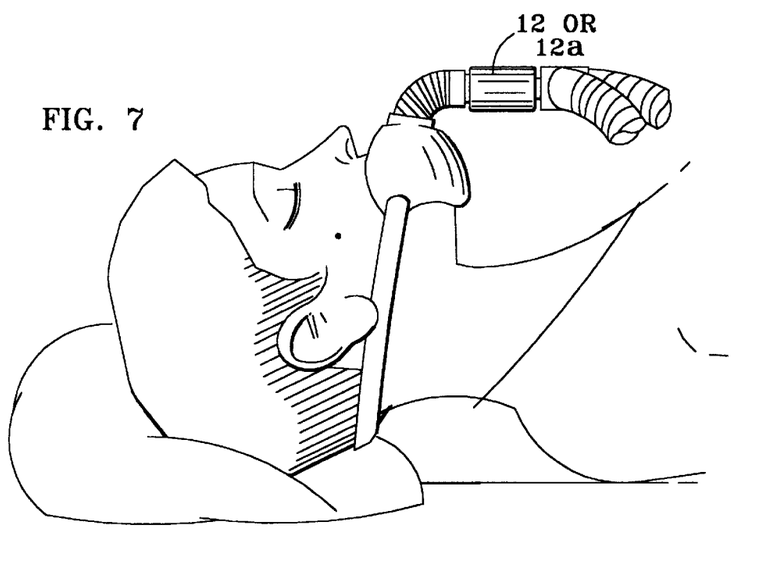
FIG. 7 shows a possible location of either a one or two-way apparatus in series in the breathing circuit of a patient having an artificial airway.
Figure 8:
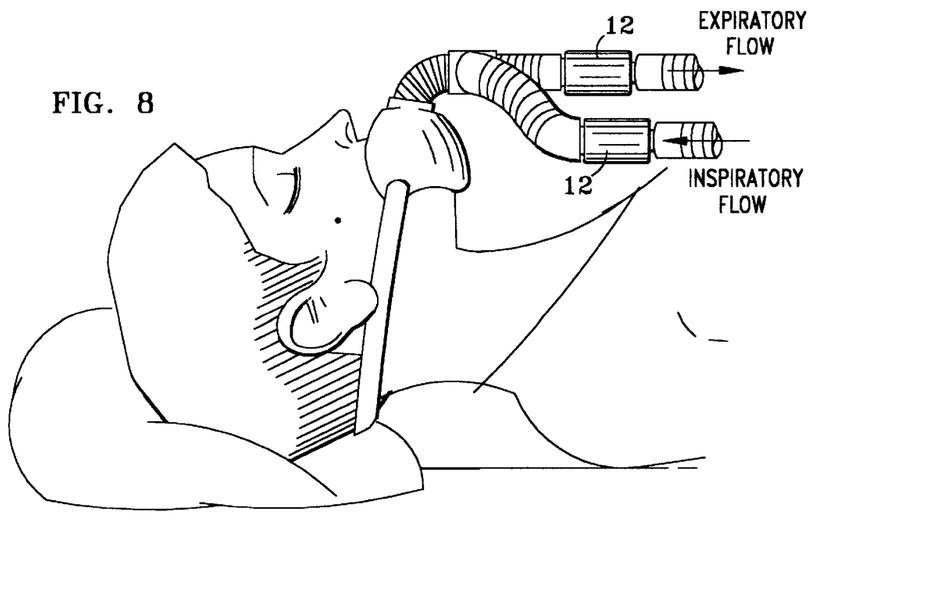
FIG. 8 shows possible locations of separate one-way apparati, one in series in the inspiratory branch and one in series in the expiratory branch of the breathing circuit.

FIGS. 7 and 8 show possible placements of apparatus of the present invention. FIG. 7 shows where either a one way sensing apparatus using one-sensor adapter 12, or a two way sensing apparatus with two-sensor adapter 12a, could be placed in series in a patient's artificial airway at the proximal end of the airway, just before the airway enters the patient. FIG. 8 shows placement of two one way sensing adapters 12, one adapter placed in series in the inspiratory branch of a breathing circuit, and another placed in series in the expiratory branch of the breathing circuit.

Figure 9:
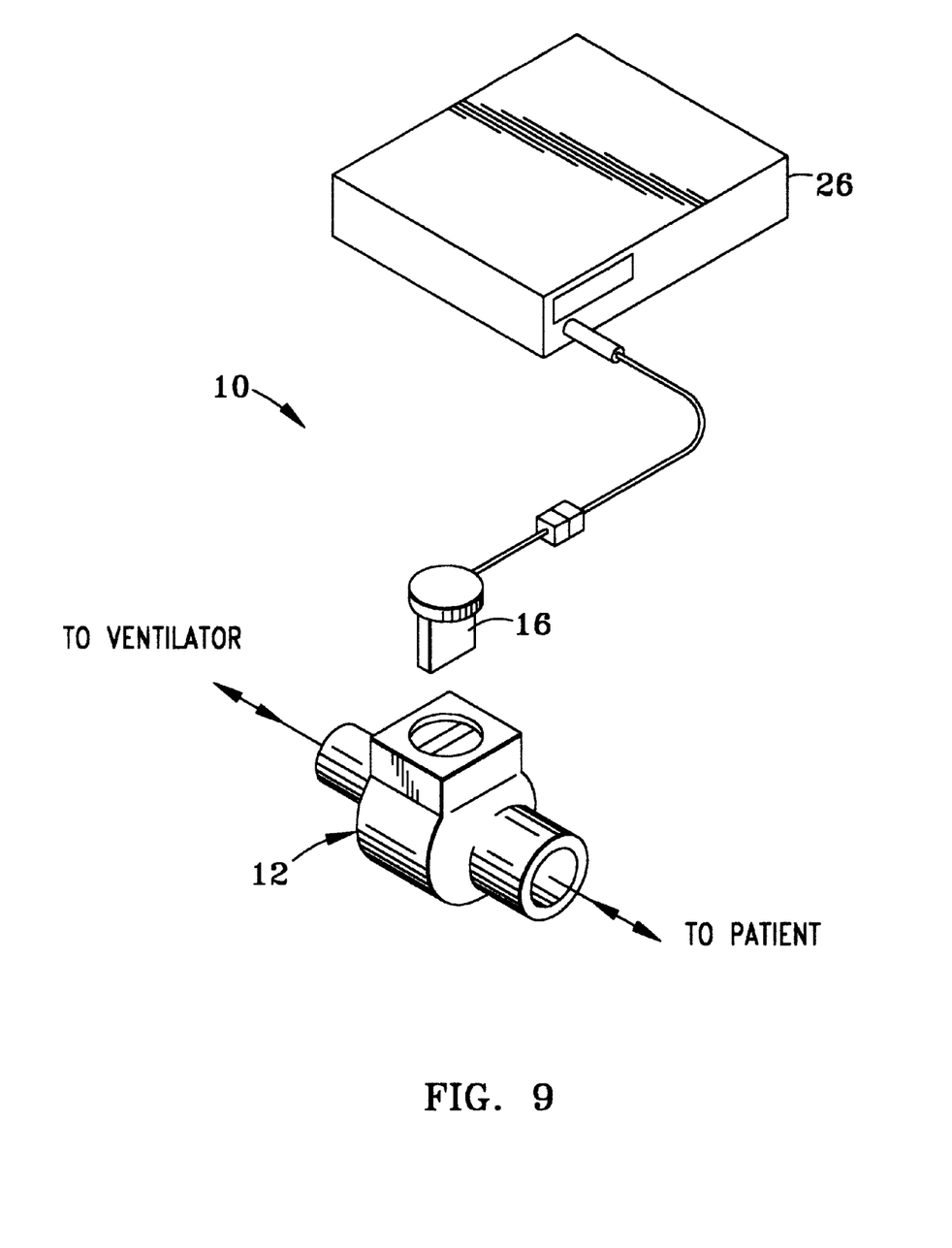
FIG. 9 is a perspective view of another embodiment of the present invention in which the sensor is oriented perpendicular to the direction of the flow of air through the adapter.

FIG. 9 shows another possible embodiment of the invention, 10b, showing a different orientation of sensing device 16 incorporatable into a one-sensor adapter 12 wherein sensing device 16 is oriented perpendicular to the direction of the flow of air through the adapter. In the previously shown embodiments, the sensing device was oriented parallel to the direction of air flow through the humidity sensing chamber. It is also possible to incorporate two perpendicularly oriented sensing devices into an adapter although this is not shown.

Sensing device 16 should preferably include a low-cost, polymer capacitive or resistance based sensor 17 that has interchangeability calibration of about 3%. Sensing device 16 should be able to operate in a 100% condensing environment, which exists in breathing circuits, without drift. Thus, the sensor system of the present invention can monitor humidity levels from 0–100%. The preferable operating temperature range for using sensing device 16 is between –40 to +212 degrees Fahrenheit which range includes breathing circuit temperatures of +80 to +110 degrees Fahrenheit. Sensing device 16 is a single—use, disposable product which may be but need not be provided sterile. The sensing device provides continuous or intermittent humidity or moisture values, or trend of inspiratory gas. A particular type of sensor that may be used with the present invention is the G-CAP (R) capacitive relative humidity sensor produced by the General Eastern company of Woburn, Mass. As non-limiting examples, other types of sensing devices which can be used in the present invention include: the EMD-2000 micro relative humidity sensor of PHYS-CHEM SCIENTIFIC CORP. of N.Y., N.Y., the INTERCAP (R) sensor of the Vaisala company, the IC Humidity Sensor IH-3605 of the HyCal company of El Monte, Calif.

A type of membrane material usable with the present invention is a Gore-Tex (R) brand selectively permeable porous sheet material comprised of polytetrafluoroethylene (PTFE) based on ICI's Fluon (R) brand PTFE. The material is selectively permeable to air and water vapor and is a three-dimensional matrix of nodes and interconnecting fibrils of 100 percent PTFE. Another possible material for the membrane is DuPont's TYVEK(R) brand spunbonded olefin material manufactured from very fine continuous filaments of high density polyethylene bonded together by heat and pressure. The material of the membrane should be selectively permeable to air and water vapor but exclude other materials.

Monitors which may be used as the reporting means of the present invention, with modification if necessary to be adapted for use with humidity sensing devices of the present invention, may by way of non-limiting example include monitors such as: the Model 880 pocket size RH and Temperature indicator of the General Eastern company, the HMI 31 portable monitor of the Vaisala company, or the HM34 pocket size relative humidity and temperature indicator of the Vaisala company.

In order to perhaps optimize monitor performance with the present invention, adjustments in or design changes could be made to existing monitor technology in order to produce a monitor that is particularly suited to reporting humidity and/or temperature readings and trends in the airway of a patient with an artificial airway.

In the method of monitoring and delivering humidity of the present invention, in the embodiment shown in FIG. 1, a clinician connects the adapter 12 in series with the breathing circuit and the artificial airway. Then the cable 24 is connected. Finally, the portable monitor 26 may be connected to cable 24 to get a reading of humidity (absolute and/or relative), and temperature so that a clinician can record the data on the patient's chart. If adjustments in humidity are required, they may be made while continuously monitoring. Monitor 26 may be disconnected from sensor end cable segment 24a of one patient's system, and be connected to another patient's system for reading and data recording. It is also possible to leave a monitor connected to a patient's system for longer term continuous monitoring. For use with longer term monitoring, the monitor may be equipped with minimum and maximum humidity level alarms which would sound should a patient's humidity fall below a set minimum, or rise above a set maximum. In other embodiments, data logging and print out capabilities are possible so that measurements would not have to be manually recorded by a clinician. Also in other embodiments, the method could include a feedback loop mechanism that would automatically adjust the amount of moisture supplied to a patient based on the measurements provided by the sensing device. The feedback mechanism may be one similar to that used in the field of Heat Ventilation and Air Conditioning (HVAC) applications which automatically adjusts humidity of a room, building, or enclosure.

The goal of this system/apparatus 10 is to be able to deliver reliably and accurately about 30 ml of water/liter of gas at 31–35 degrees C., such that the relative humidity of gases reaching a patient's distal airways is 100%. For the most part today, it is difficult to consistently deliver adequate, appropriate levels of moisture, and therefore appropriate moisture levels are not delivered, or not delivered consistently. The present invention, makes it easier to measure, monitor and trend moisture levels, and thus adjust delivered moisture appropriately to yield the desired humidity.

The present invention and many of its attendant advantages are understood from the foregoing description and it will be apparent that various changes may be made in the form, construction and arrangement of the parts thereof without departing from the spirit and scope of the invention or sacrificing its material advantages, the form hereinbefore described being merely a preferred or exemplary embodiment thereof.

I claim:

1. An apparatus for sensing the humidity of gases present in a patient having an artificial airway, said apparatus comprising:
    an adapter having a wall defining at least one humidity sensing chamber therein;
    means for connecting said adapter, in an inspiratory limb of a breathing circuit of said artificial airway in gas flow communication with said humidity sensing chamber, and
    a humidity sensing device incorporated into at least one of said at least one humidity sensing chamber, said humidity sensing device being an Rh sensor element in humidity sensing communication with said gases.

2. The apparatus for sensing the humidity of gases according to claim 1 further comprising means for attaching said adapter, in gas flow communication with said humidity sensing chamber, to a ventilation circuit.

3. The apparatus for sensing the humidity of gases according to claim 1 wherein said humidity sensing device comprises said Rh sensor element being contained in a sensor housing.

4. The apparatus for sensing the humidity of gases according to claim 2 wherein said humidity sensing device comprises said Rh sensor element being contained in a sensor housing.

5. The apparatus for sensing the humidity of gases according to claim 3 wherein said humidity sensing device further comprises means for communicating humidity information from said humidity sensing element.

6. The apparatus for sensing the humidity of gases according to claim 4 wherein said humidity sensing device further comprises means for communicating humidity information from said humidity sensing element.

7. The apparatus for sensing the humidity of gases according to claim 5 wherein said humidity information communicated from said humidity sensing device is in the form of signals selected from the group consisting of electrical, light and radio frequency.

8. The apparatus for sensing the humidity of gases according to claim 6 wherein said humidity information communicated from said humidity sensing device is in the form of signals selected from the group consisting of electrical, light and radio frequency.

9. The apparatus for sensing the humidity of gases according to claim 5 further comprising means for receiving and translating said humidity information communicated from said humidity sensing device and reporting to a user.

10. The apparatus for sensing the humidity of gases according to claim 6 further comprising means for receiving and translating said humidity information communicated from said humidity sensing device and reporting to a user.

11. The apparatus for sensing the humidity of gases according to claim 9 wherein said means for communicating humidity information from said humidity sensing element comprises electrical contacts for electrically connecting each said at least one humidity sensing device to said means for receiving and translating said humidity information.

12. The apparatus for sensing the humidity of gases according to claim 10 wherein said means for communicating humidity information from said humidity sensing element comprises electrical contacts for electrically connecting each said at least one humidity sensing device to said means for receiving and translating said humidity information.

13. The apparatus for sensing the humidity of gases according to claim 1 wherein said means for connecting said adapter to said artificial airway is a connection configured to be compatible with a standard artificial airway connection.

14. The apparatus for sensing the humidity of gases according to claim 2 wherein said means for attaching said adapter to said ventilation circuit is a connection configured to be compatible with a standard ventilation circuit connection.

15. The apparatus for sensing the humidity of gases according to claim 1 further comprising at least one water vapor permeable membrane positioned and attached in a manner to separate said humidity sensing device from said gases in said least one humidity sensing chamber and such that said humidity sensing device detects the moisture passing through each said at least one water vapor permeable membrane.

16. The apparatus for sensing the humidity of gases according to claim 2 further comprising at least one water vapor permeable membrane positioned and attached in a manner to separate said humidity sensing device from said gases in said least one humidity sensing chamber and such that said humidity sensing device detects the moisture passing through each said at least one water vapor permeable membrane.

17. The apparatus for sensing the humidity of gases according to claim 1 wherein said humidity sensing device is formed integral with said wall defining said at least one humidity sensing chamber therein of said adapter.

18. The apparatus for sensing the humidity of gases according to claim 10 further comprising at least one temperature sensing device wherein said at least one temperature sensing device further comprises:

means for communicating temperature information from said temperature sensing device;

means for receiving and translating said temperature information communicated from said temperature sensing device and reporting to a user.

19. The apparatus for sensing the humidity of gases according to claim 1 wherein said at least one humidity sensing chamber is two chambers, a first humidity sensing chamber, a second humidity sensing chamber, and a means for air-flow isolating said first humidity sensing chamber from said second humidity sensing chamber.

20. The apparatus for sensing the humidity of gases according to claim 19 wherein said means for air-flow isolating comprises:

a dividing portion;

a first one-directional valve disposed at said first humidity sensing chamber; and a second one-directional valve disposed at said second humidity sensing chamber, wherein each said first and second one-directional valve further disposed such that gases pass through said first humidity sensing chamber in one direction and gases pass through said second humidity sensing chamber in an opposite direction.

21. The apparatus for sensing the humidity of gases according to claim 20 wherein each said first humidity sensing chamber and said second humidity sensing chamber has a first humidity sensing device incorporatable into said first humidity sensing chamber and a second humidity sensing device incorporatable into said second humidity sensing chamber.

22. The apparatus for sensing the humidity of gases according to claim 10 wherein said means for receiving and translating said humidity information further comprises a minimum level humidity alarm and a maximum level humidity alarm wherein said minimum level humidity alarm is sounded when a detected humidity falls below a determined minimum level, and wherein said maximum level humidity alarm is sounded when a detected humidity rises above a determined maximum level.

23. The apparatus for sensing the humidity of gases according to claim 10 wherein said means for receiving and translating said humidity information further comprises means to automatically adjust a moisture delivery system such that delivery of moisture to a patient is automatically regulated by said means to automatically adjust in response to humidity and moisture content measurements obtained by said humidity sensing device.

24. A method for monitoring the humidity of gases in a patient having an artificial airway, said method comprising the steps of:

securing an adapter in humidity sensing communication with a patient's artificial airway in an inspiratory limb of a breathing circuit of said artificial airway and with a ventilation circuit, said adapter having at least one humidity sensing chamber therein;

attaching at least one Rh sensor humidity sensing device to said adapter;

placing a means for receiving and translating humidity information communicated from each said humidity sensing device and reporting to a user, said means for receiving and translating receives signals from said humidity sensing device and translates and reports the signals;

monitoring said signals and responding to said signals to increase or decrease moisture delivered to a patient; and trending the Rh of these inspiratory gases allowing the use of said Rh sensor technology.

25. The method for monitoring the humidity of gases in a patient according to claim 24 wherein said method further comprises the step of securing at least one temperature sensing device to said adapter and measuring the temperature of gases passing through said adapter.

26. The method for monitoring the humidity of gases in a patient according to claim 24 wherein said adapter comprises a first humidity sensing chamber through which inspired or delivered air passes, and a second humidity sensing chamber through which expired air passes, and which second humidity sensing chamber is air-flow isolated from said first humidity sensing chamber; further comprising the steps of:

attaching a first humidity sensing device to said first humidity sensing chamber;

attaching a second humidity sensing device to said second humidity sensing chamber; and measuring and reporting, moisture content and relative humidity of air passing through said first and said second humidity sensing chambers such that both the inspiratory and expiratory gases are monitored.

27. The method for monitoring the humidity of gases in a patient of claim 24 further comprising connecting one of said apparatus in humidity sensing communication along the inspiratory branch of a breathing circuit, and connecting a second of said apparatus in humidity sensing communication along the expiratory branch of the breathing circuit such that both inspired and expired gases are monitored and reported separately.

28. An apparatus for monitoring humidity in a patient with an artificial airway comprising an Rh sensor humidity sensing device incorporated in an inspiratory limb of a breathing circuit of said artificial airway in humidity sensing communication with the patient's airflow thereby monitoring the humidity of inspired gas delivered to the patient.

29. A method for monitoring humidity in a patient with an artificial airway comprising the steps of installing an Rh sensor humidity sensing device selected from the group consisting of capacitive type and resistive type of Rh sensor technology, in an inspiratory limb of a breathing circuit of said artificial airway in humidity sensing communication with the patient's airflow;

monitoring humidity readings of inspired gas delivered to the patient taken by said Rh sensor humidity sensing device; and trending the Rh of these inspiratory gases allowing the use of said capacitive type and resistive type of Rh sensor technology.

* * * * *